United States Patent [19]
Walker

[11] Patent Number: 4,935,435
[45] Date of Patent: Jun. 19, 1990

[54] USE OF TETRAZOLE DERIVATIVES

[75] Inventor: Joyce L. Walker, Brentwood, England

[73] Assignee: May & Baker Limited, Dagenham, England

[21] Appl. No.: 335,551

[22] Filed: Apr. 10, 1989

[30] Foreign Application Priority Data

Apr. 11, 1988 [GB] United Kingdom ................ 8808476
May 27, 1988 [GB] United Kingdom ................ 8812698

[51] Int. Cl.$^5$ ............................................. A61K 31/41
[52] U.S. Cl. ................................................... 514/381
[58] Field of Search ........................................ 514/381

Primary Examiner—Stanley J. Friedman
Attorney, Agent, or Firm—Stevens, Davis, Miller & Mosher

[57] ABSTRACT

The invention provides a method for the treatment of a human or animal patient suffering from, or subject to, an arthritic or related autoimmune disorder, a connective tissue disorder or transplant rejection, using a compound which is a tetrazole derivative of the formula:

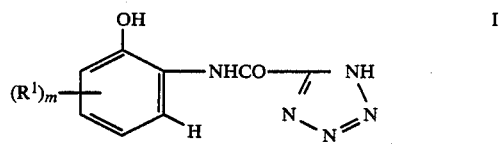

wherein $R^1$ represents halogen, alkyl, alkoxy, alkylthio, alkylsulphinyl, alkylsulphonyl, alkylsulphamoyl, dialkylsulphamoyl, dialkylamino, dialkylcarbamoyl, alkanoyl, alkoxycarbonyl, alkoxycarbonylamino, alkylcarbamoyl, alkanoylamino, cycloalkylcarbonyl, hydroxy, formyl, nitro, trifluoromethyl, trifluoroacetyl, aryl, benzyloxycarbonylamino, amino, sulphamoyl, cyano, tetrazol-5-yl, carboxy, carbamoyl, benzyloxy, aralkanoyl, aroyl, or a group of the formula —$CR^2$=$NOR^3$ wherein $R^2$ represents hydrogen, alkyl, aryl, aralkyl, trifluoromethyl or cycloalkyl, and $R^3$ represents hydrogen, alkyl, optionally substituted by phenyl, or represents optionally substituted aryl and m represents zero, 1, 2 or 3, or a pharmaceutically acceptable salt thereof.

10 Claims, No Drawings

USE OF TETRAZOLE DERIVATIVES

This invention relates to tetrazole-5-carboxanilides, and pharmaceutical compositions prepared from the same, for use in a new method of treatment of the human or animal body.

In British Patent Specification No. 2006782B and in the specifications of corresponding patents and patent applications filed outside Great Britain, for example U.S. Pat. No. 4442115, there are described inter alia compounds of the general formula I at the end of the present specification [wherein $R_1$ represents a halogen (i.e. fluorine, chlorine, bromine or iodine) atom or a straight- or branched-chain alkyl, alkoxy, alkylthio, alkylsulphinyl, alkylsulphonyl, or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl, alkoxycarbonylamino, alkylcarbamoyl or alkanoylamino group containing from 2 to 6 carbon atoms, a cycloalkylcarbonyl group containing from 3 to 8 carbon atoms in the cycloalkyl moiety, or a hydroxy, formyl, nitro, trifluoromethyl, trifluoroacetyl, aryl (e.g. phenyl), benzyloxycarbonylamino, amino, sulphamoyl, cyano, tetrazol-5-yl, carboxy, carbamoyl, benzyloxy, aralkanoyl (e.g. phenylacetyl), or aroyl (e.g. benzoyl) group, or a group of the formula:

$$-CR^2 = NOR^3 \quad \text{II}$$

(wherein $R^2$ represents a hydrogen atom or a straight- or branched-chain alkyl group containing from 1 to 5 carbon atoms, an aryl (e.g. phenyl), aralkyl (e.g. benzyl) or trifluoromethyl group, or a cycloalkyl group containing from 3 to 8 carbon atoms, and $R^3$ represents a hydrogen atom, or a straight- or branched-chain alkyl group containing from 1 to 6 carbon atoms optionally substituted by a phenyl group, or represents an aryl (e.g. phenyl) group optionally substituted by one or more substituents selected from halogen atoms and straight- or branched-chain alkyl and alkoxy groups containing from 1 to 6 carbon atoms and hydroxy, trifluoromethyl and nitro groups), and m represents zero or an integer 1, 2 or 3, preferably 1 or 2, the substituents $R^1$ being the same or different when m represents 2 or 3] and pharmaceutically acceptable salts thereof, processes for their preparation and pharmaceutical compositions containing them.

It will be understood by those skilled in the art that each of the hydrogen atoms depicted in general formula I in the moieties OH, NHCO and NH may give rise to tautomerism and that all the resulting tautomeric forms may be present to a greater or lesser degree and are in a state of dynamic equilibrium with each other. Furthermore the substituents $R^1$, $R^2$ and $R^3$ may contain chiral centres and thus give rise to optical isomerism and the group of formula II may be in the syn or anti configuration. The present invention embraces all optical and geometrical isomers of general formula I and all tautomers of compounds of formula I and mixtures thereof.

The aforementioned specifications disclose that the compounds of formula I possess valuable pharmacological properties, in particular properties of value in the treatment of allergic conditions, for example respiratory disorders such as those manifested by the interaction of tissue-fixed antibodies with specific antigens, such as allergic bronchial asthma.

As a result of research and experimentation it has now been found that the compounds of formula I possess properties which are indicative of utility in the treatment of arthritic disorders and related autoimmune disorders, such as rheumatoid arthritis, osteoarthritis, seronegative arthritides such as ankylosing spondylitis, psoriatic arthritis and enteropathic arthropathy, connective tissue disorders such as systemic lupus erythematosus and polymyotis, and the tendency to rejection of transplants.

In particular, in laboratory tests, compounds of formula I have been shown to inhibit the deterioration of joints in rodents' limbs, but not to inhibit cyclo-oxygenase.

This profile of activity is considered particularly important when contrasted with compounds currently employed in the treatment of arthritic disorders, which are primarily antiinflammatories and do not possess the said ability to inhibit joint deterioration in man.

A class of compounds of general formula I which is important includes those compounds wherein $R^1$ represents a halogen atom or a straight- or branched-chain alkyl, alkoxy, or alkylsulphonyl group, each such group containing from 1 to 4 carbon atoms, a dialkylcarbamoyl group (wherein the two groups may be the same or different and each contains 1 or 2 carbon atoms), a straight- or branched-chain alkanoyl, alkoxycarbonyl, or alkanoylamino group containing from 2 to 4 carbon atoms, a cycloalkylcarbonyl group containing from 3 to 6 carbon atoms in the cycloalkyl moiety, or a nitro, trifluoroacetyl, amino, cyano, or phenylacetyl group or a group of formula II (wherein $R^2$ represents a straight- or branched-chain alkyl group containing from 1 to 3 carbon atoms, and $R^3$ represents a hydrogen atom or a straight- or branched-chain alkyl group containing from 1 to 3 carbon atoms), and m represents zero or an integer 1 or 2, the substituents $R^1$ being the same or different when m represents 2, and their pharmaceutically acceptable salts.

Especially important are those compounds of formula I wherein $R^1$ represents a fluorine or bromine atom or a methyl, ethyl, propyl, methoxy, methylsulphonyl, dimethylcarbamoyl, acetyl, propionyl, butyryl, isobutyryl, methoxycarbonyl, ethoxycarbonyl, acetylamino, cyclopropylcarbonyl, nitro, trifluoroacetyl, amino, cyano, phenylacetyl, 1-(hydroxyimino)ethyl or 1-(methoxyimino)ethyl group, and m represent zero or an integer 1 or 2, the substituents $R^1$ being the same or different when m represents 2, and their pharmaceutically acceptable salts.

The class of compounds of general formula I wherein the benzene ring carries at least one substituent $R^1$ and $R^1$ represents a straight- or branched-chain alkoxy group containing from 1 to 4 carbon atoms or a straight- or branched-chain alkanoyl or alkoxycarbonyl group containing from 2 to 4 carbon atoms, or a group of formula II (wherein $R^2$ and $R^3$ are as hereinbefore defined), preferably in the 3-position of the benzene ring (i.e. attached to the carbon atom ortho to the carbon atom with a hydroxy substituent attached thereto), any other substituents $R^1$ present being as hereinbefore defined, and their pharmaceutically acceptable salts, are of great importance.

Compounds of general formula I wherein the benzene ring carries at least one substituent $R^1$ and $R^1$ represents a straight- or branched-chain alkanoyl group containing from 2 to 4 carbon atoms, preferably in the 3-position of the benzene ring, any other substituents $R^1$ being as hereinbefore defined, and their pharmaceutically acceptable salts, are of outstanding importance.

3'-Acetyl-5'-fluoro-2'-hydroxytetrazole-5-carboxanilide, hereinafter referred to as "compound A", whose formula is shown in FIG. III, is of particular importance.

For example, in tests compound A inhibited erosion and inflammation caused by collagen-induced arthritis in rats at oral doses of 30 mg/kg body weight per day, when compared with control animals.

Joint sizes were measured periodically, for 70 days, by means of electronic calipers placed across the tibiotarsal junction. Although the mean joint diameter in the control animals increased from 7.6 mm to 8.1 mm over the 70 days the mean joint diameter in the treated animals only increased to 7.7 mm.

On the 71st day the hind paws were examined by X-radiography. Joint damage was assessed according to five parameters and scored on an arbitrary scale of 0 to 5. For each of the five parameters the joints of the control animals were more severely damaged than those of the treated animals.

The utility of the compounds of formula I is enhanced by the fact that they are only of very low toxicity to mammals.

For example, in the rat the oral $LD_{50}$ is greater than 4,000 mg/kg. In the mouse the oral $LD_{50}$ is between 2,500 and 5,000 mg/kg and the intravenous LD50 is 380mg/kg.

Compound A and other compounds of general formula I can be prepared by processes described in the aforementioned specifications.

The present invention provides a compound of the formula shown in FIG. I, or a pharmaceutically acceptable salt thereof, for use in the preparation of a pharmaceutical composition for the treatment of a condition selected from arthritic disorders and related autoimmune disorders, such as rheumatoid arthritis, osteoarthritis, seronegative arthritides such as ankylosing spondylitis, psoriatic arthritis and enteropathic arthropathy, connective tissue disorders such as systemic lupus erythematosus and polymyotis, and the tendency to rejection of transplants.

The present invention also provides a method for the treatment of a human or animal patient suffering from, or subject to, a condition selected from arthritic disorders and related autoimmune disorders, such as rheumatoid arthritis, osteoarthritis, seronegative arthritides such as ankylosing spondylitis, psoriatic arthritis and enteropathic arthropathy, connective tissue disorders such as systemic lupus erythematosus and polymyotis, and the tendency to rejection of transplants which comprises administering to the patient an effective amount of a compound of the formula shown in FIG. I, or a pharmaceutically acceptable salt thereof to secure an improvement in the condition of the patient.

The present invention also provides a compound of the formula shown in FIG. I, or a pharmaceutically acceptable salt thereof, and a pharmaceutical composition containing the same, for use in a new method of treatment of the human or animal body by therapy in the treatment of a condition selected from arthritic disorders and related autoimmune disorders, such as rheumatoid arthritis, osteoarthritis, seronegative arthritides such as ankylosing spondylitis, psoriatic arthritis and enteropathic arthropathy, connective tissue disorders such as systemic lupus erythematosus and polymyotis, and the tendency to rejection of transplants.

The pharmaceutical compositions for use in this method, and the means of administration, are similar to those described in the aforementioned specifications.

The oral route of administration is especially preferred.

The dose of the compounds of general formula I employed depends upon the desired therapeutic effect, the condition of the patient, the route of administration and the duration of the treatment. In the adult, the doses are generally between 0.1 and 1000, preferably between 1 and 100, mg per day, especially when administered orally.

Compositions in the form of solutions or suspensions, if desired together with additives as described above, in vegetable or other greases, paraffin or other waxes or lacquers or creams, to be applied topically, are included in the invention.

Compositions for topical administration generally contain up to 5 percent, preferably from 0.1 to 3.0 percent, by weight of active ingredient, and they are normally applied up to 4 times per day.

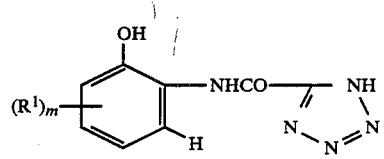

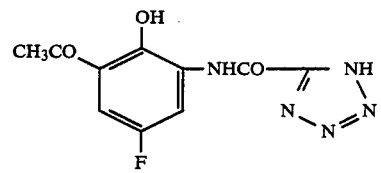

We claim:

1. A method for the treatment of a human or animal patient suffering from, or subject to, an arthritic or related autoimmune disorder, a connective tissue disorder or transplant rejection, which comprises the administration to said human or animal patient of an effective amount of a compound which is a tetrazole derivative of the general formula:

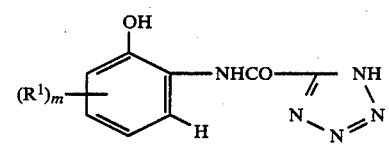

wherein $R^1$ represents a halogen atom or a straight- or branched-chain alkyl, alkoxy, alkylthio, alkylsulphinyl, alkylsulphonyl, or alkylsulphamoyl group, each such group containing from 1 to 6 carbon atoms, a dialkylsulphamoyl, dialkylamino or dialkylcarbamoyl group where the two alkyl groups, which may be the same or different, each contain from 1 to 4 carbon atoms, a straight- or branched-chain alkanoyl, alkoxycarbonyl, alkoxycarbonylamino, alkylcarbamoyl or alkanoylamino group containing from 2 to 6 carbon atoms, a cycloalkylcarbonyl group containing from 3 to 8 carbon atoms in the cycloalkyl moiety, or a hydroxy, formyl, nitro, trifluoromethyl, trifluoroacetyl, aryl, benzyloxycarbonylamino, amino, sulphamoyl, cyano, tetrazol-5-yl, carboxy, carbamoyl, benzyloxy, aralkanoyl or aroyl group, or a group of the formula:

$$-CR^2=NOR^3 \qquad \text{II}$$

wherein $R^2$ represents a hydrogen atom or a straight- or branched-chain alkyl group containing from 1 to 5 carbon atoms, an aryl, aralkyl or trifluoromethyl group, or a cycloalkyl group containing from 3 to 8 carbon atoms, and $R^3$ represents a hydrogen atom, or a straight- or branched-chain alkyl group containing from 1 to 6 carbon atoms optionally substituted by a phenyl group, or represents an aryl group optionally substituted by one or more substituents selected from halogen atoms and straight- or branched-chain alkyl and alkoxy groups containing from 1 to 6 carbon atoms and hydroxy, trifluoromethyl and nitro groups, and m represents zero or an integer 1, 2 or 3, the substituents $R^1$ being the same or different when m represents 2 or 3, or a pharmaceutically acceptable salt thereof.

2. A method according to claim 1 wherein $R^1$ represents a halogen atom or a straight- or branched-chain alkyl, alkoxy, or alkylsulphonyl group, each such group containing from 1 to 4 carbon atoms, a dialkylcarbamoyl group where the two alkyl groups, which may be the same or different, each containing 1 to 2 carbon atoms, a straight- or branched-chain alkanoyl, alkoxycarbonyl, or alkanoylamino group containing from 2 to 4 carbon atoms, a cycloalkylcarbonyl group containing from 3 to 6 carbon atoms in the cycloalkyl moiety, or a nitro, trifluoroacetyl, amino, cyano, or phenylacetyl group or a group of formula II as defined in claim 1 wherein $R^2$ represents a straight- or branched-chain alkyl group containing from 1 to 3 carbon atoms, and $R^3$ represents a hydrogen atom or a straight- or branched-chain alkyl group containing from 1 to 3 carbon atoms, and m represents zero or an integer 1 or 2, the substituents $R^1$ being the same or different when m represents 2.

3. A method according to claim 1 wherein $R^1$ represents a fluorine or bromine atom or a methyl, ethyl, propyl, methoxy, methylsulphonyl, dimethylcarbamoyl, acetyl, propionyl, butyryl, isobutyryl, methoxycarbonyl, ethoxycarbonyl, acetylamino, cyclopropylcarbonyl, nitro, trifluoroacetyl, amino, cyano, phenylacetyl, 1-(hydroxyimino)ethyl or 1-(methoxyimino)ethyl group, and m represents zero or an integer 1 or 2, the substituents $R^1$ being the same or different when m represents 2.

4. A method according to claim 1 wherein m>0 and $R^1$ represents a straight- or branched-chain alkoxy group containing from 1 to 4 carbon atoms or a straight- or branched-chain alkanoyl or alkoxycarbonyl group containing from 2 to 4 carbon atoms, or a group or formula II as defined in claim 1 wherein $R^2$ and $R^3$ are as hereinbefore defined, any other substituents $R^1$ present being as hereinbefore defined.

5. A method according to claim 1 wherein the tetrazole derivative is 3'-acetyl-5'-fluoro-2'-hydroxytetrazole-5-carboxanilide.

6. A method according to claim 1 in which the compound is administered orally.

7. A method according to claim 1 in which the compound is administered topically.

8. A method according to claim 1 wherein the daily dose of the compound is from 0.1 to 1000 mg.

9. A method according to claim 8 wherein the daily dose of the compound is from 1 to 100 mg.

10. A method according to claim 1 for the treatment of a human or animal patient suffering from, or subject to, rheumatoid arthritis, osteoarthritis, ankylosing spondylitis, psoriatic arthritis, enteropathic arthropathy, systemic lupus erythematosus or polymyotis.

* * * * *